United States Patent
Liu et al.

(10) Patent No.: US 11,313,781 B2
(45) Date of Patent: Apr. 26, 2022

(54) SELF-PARATIVE CALIBRATION METHOD OF AN APTAMER SENSOR

(71) Applicant: ZiO Health Ltd., London (GB)

(72) Inventors: Yu Liu, London (GB); Shaolin Liang, Hong Kong (HK); Rory Ryan, Tunbridge Wells (GB)

(73) Assignee: ZiO Health Ltd.

( * ) Notice: Subject to any disclaimer, the term of this patent is extended or adjusted under 35 U.S.C. 154(b) by 0 days.

(21) Appl. No.: 17/309,321

(22) PCT Filed: Nov. 19, 2019

(86) PCT No.: PCT/IB2019/059923
§ 371 (c)(1),
(2) Date: May 19, 2021

(87) PCT Pub. No.: WO2020/104934
PCT Pub. Date: May 28, 2020

(65) Prior Publication Data
US 2021/0364406 A1  Nov. 25, 2021

Related U.S. Application Data

(60) Provisional application No. 62/769,038, filed on Nov. 19, 2018.

(51) Int. Cl.
*G01N 15/06* (2006.01)
*G01N 27/327* (2006.01)
(Continued)

(52) U.S. Cl.
CPC ..... *G01N 15/0656* (2013.01); *G01N 15/0606* (2013.01); *G01N 27/3277* (2013.01); *G01N 33/5438* (2013.01); *G01N 2015/0065* (2013.01)

(58) Field of Classification Search
None
See application file for complete search history.

(56) References Cited

U.S. PATENT DOCUMENTS

2011/0139636 A1   6/2011   Lai et al.

FOREIGN PATENT DOCUMENTS

WO   2009055224 A1   4/2009
WO   2018058028 A2   3/2018
(Continued)

OTHER PUBLICATIONS

Hui Li et al: "Calibration-Free Electrochemical Biosensors Supporting Accurate Molecular Measurements Directly in Undiluted Whole Blood," Journal of the American Chemical Society, vol. 139, No. 32, Aug. 16, 2017, pp. 11207-11213, XP055663955, ISSN: 0002-7863, DOI: 10.1021/jacs.7b05412.
(Continued)

*Primary Examiner* — J. Christopher Ball
(74) *Attorney, Agent, or Firm* — Rosenthal IP Law; Lawrence Rosenthal

(57) ABSTRACT

A method for using a biosensor to determine the concentration of a target analyte, that does not require a pre-test calibration step. Small variations between electrodes on different biosensors, even when the biosensors are designed to be identical and manufactured in as close a manner as possible, can lead to significant variations in output when the electrochemical method is applied. Therefore, existing biosensors are calibrated before use, either during manufacturing or just prior to use. Prior calibration is not feasible for disposable applications, and increases the complexity of use if required to be performed by the end-user. A self-parative calibration method is described in which certain constants
(Continued)

are determined during testing of the biosensor, then applied to all uses of the biosensor, so that an additional calibration step is not required.

7 Claims, 4 Drawing Sheets

(51) Int. Cl.
　　*G01N 33/543*　　(2006.01)
　　*G01N 15/00*　　(2006.01)

(56) References Cited

FOREIGN PATENT DOCUMENTS

| WO | 2018223024 A2 | 12/2018 |
| WO | 2019089465 A1 | 5/2019 |

OTHER PUBLICATIONS

Qingcui Xu Et Al: "Ratiometric electrochemical aptasensor based on ferrocene and carbon nanofibers for highly specific detection of tetracycline residues", Scientific Reports, vol. 7, No. 1, Nov. 7, 2017, XP055663963, DOI: 10.1038/s541598-017-15333-5.

Caixia Zhu et al.: "A new electrochemical aptasensor for sensitive assay of a protein based on the dual-signaling electrochemical ratiometric method and DNA walker strategy", Chemical Communications, vol. 54, No. 73, Jan. 1, 2018, p. 10359-10362, XP055663965, UK, ISSN: 1359-7345, DOI: 10.1039/C8CC05829F.

Renny Edwin Fernandez et al: "Disposable aptamer-sensor aided by magnetic nanoparticle enrichment for detection of salivary cortisol variations in obstructive sleep apnea patients", Scientific Reports, vol. 7, No. 1, Dec. 1, 2017, XP55663967, DOI: 10.1038/S41598-017-17835-8.

Hui Li et al., "Calibration-free electrochemical biosensors supporting accurate molecular measurements directly in undiluted whole blood", Journal of the American Chemical Society, Jul. 16, 2017, DOI: 10.1021/jacs.7b05412.

Hui Li at al, "Supporting Information for 'Calibration-free electrochemical biosensors supporting accurate molecular measurements directly in undiluted whole blood.'"

Juan Liu et al., "Achieving Reproducible Performance of Electrochemical, Folding Aptamer-Based Sensors on Microelectrodes: Challenges and Prospects", Analytical Chemistry, vol. 86, No. 22, pp. 11417-11424, Oct. 22, 2014, DOI: 10.1021/ac503407e.

Alexander P. Demchenko, "The problem of self-calibration of fluorescence signal in microscale sensor systems", The Royal Society of Chemistry, Lab Chip, vol. 5, Sep. 27, 2005, pp. 1210-1223, DOI: 10.1039/b507447a.

SELF-PARATIVE CALIBRATION METHOD OF AN APTAMER SENSOR

CROSS-REFERENCE TO RELATED APPLICATIONS

This application claims the benefit of U.S. Provisional Patent Application No. 62/769,038, filed on 19 Nov. 2018.

FIELD OF THE INVENTION

The invention lies in the field of aptamer biosensors, methods of their use, and specifically their calibration.

BACKGROUND

The electrochemical aptamer-based sensor principle is based on the coupling of target-induced conformational changes of an aptamer bioreceptor with electrochemical detection of the resulting altered charge transfer rate between the redox molecule and electrode surface. The sensor is constituted by the supporting substrate and the modified surface layer. The supporting substrate is produced from conducting materials including but not limited to gold, silver, carbon, conducting polymer or metal particle. The quality and composition of the substrate material can affect the sensor output significantly.

The electrochemical methods allow an output signal to be obtained, which becomes the input from which the analyte concentration can be calculated. The dependence of signal on analyte concentration can be represented by a calibration curve that exists for each sensor. The most commonly used calibration method is a process by which blank solution and a series of standard target solutions are tested to set up a curve of concentration versus the signal change. For example: in order to obtain the calibration curve of the sensor, the first step is to test the standard blank solution (the same solution as the target sample but not containing target), then obtain the initial blank signal, $S_0$. The second step is to test a series of standard target solutions (1, 2, 3, 4, 5 . . . ), and then equally get a series of target signals $S_t$ ($S_1$, $S_2$, $S_3$ . . . $S_n$). The third step is to calculate the signal change between each target solution and initial signal, $S_t$-$S_0$ or $S_t/S_0$-1. Using the experimental data, the calibration curve of signal change versus the target concentration, as shown in FIG. 1, can be determined. Thereafter, once the signal change is output from the electrochemical method, the analyte concentration can be calculated according to the calibration curve.

In theory, then, to obtain the signal change, there are at least two necessary parameters needed to be measured or known, one is $S_0$, also called blank signal, another one is target signal, called $S_t$. However, in the process of practical mass production, it is impossible to establish a standard calibration curve for each individual sensor and measure the $S_0$ for each sensor. While theoretically, ideal sensors of the same type have the same performance because they use the same design, materials, modification and production technology and can share one unified calibration curve, the reality is that sensor production cannot absolutely avoid the existence of electrode-to-electrode variations. Small variations can have significant influence on the accuracy of the test result if the same calibration curve is used for all sensors, even when manufactured in the same batch. For instance, FIG. 2 shows the output of a square wave voltammetry (SWV) test on two sensors of the same class that have been fabricated in as close to an identical manner as possible with current manufacturing techniques and tested in the same environmental conditions with the same target concentration, sample solution and electronic device. Voltammogram peak height is almost 50% higher in Test Strip 2 when compared to Test Strip 1, and the potential at which the peak occurs is different. The curve for Test Strip 2 is higher than Test Strip 1 because current measurements are higher across all potentials for Test Strip 2.

Hence, in order to improve result accuracy, there are two methods often considered, one is to reduce the variations between electrodes by improving the production technique as much as possible, the other is to do blank test for each individual sensor before target detection. Given that electrode-to-electrode variations are impossible to completely remove during manufacturing, what is currently practiced in commercial settings is activation of a first blank or control test that is stored within a separate reservoir and/or separate sensor within the device. The disadvantage of this method is that extra space within the device is required for a blank solution and/or extra electrodes and increased manufacturing and test strip costs. Furthermore, a point-of-use control test reduces the scalability of the product, particularly because the user must conduct or wait for the blank test to complete, increasing the possibility of user error and overall increasing the complexity of the user experience. A blank solution test makes single test, disposable applications infeasible.

Another solution is for calibration with a blank or control solution to be tested by the cartridge manufacture before shipping. However, conducting the blank test at the factory increases production costs and does not necessarily result in accuracy, due to shelf life decay and the significant possibility of very different conditions at the point of use. Thus, calibration methods are typically applied shortly before sensor use.

Currently, the most advanced calibration method known in the industry is a 'calibration-free' method proposed by Plaxco et al., WO 2018/223024 A2 ("Plaxco"). Plaxco's innovation is based on the discovery that for some aptamers a particular frequency called the non-response frequency exists whereby when utilizing the electrochemical method at the non-response frequency, the difference of signal from aptamer in bound and unbound states is in fact zero. This means that the faradic discharge current is the same when the aptamer is bound and unbound and that measured signal is independent of concentration of target. This phenomenon helps calibration of an aptamer electrochemical sensor because the sensor can be tested once at the non-response frequency and secondly at a frequency to maximize difference of signal from aptamer in bound and unbound states. The change of signal directly from target addition can be calculated in-situ without the need to first conduct a blank test on test strips in the manufacturing process.

The method relies upon the assumption that the aptamer's characteristic non-response frequency, the frequency at which measured current signal is independent of target concentration remains at one constant frequency and can be determined with accuracy. In reality, experimentation shows that the non-response frequency of the aptamer significantly shifts across a large frequency range (50 Hz-100 Hz as shown in FIG. 3) and is not completely independent of target concentration. Therefore, each test strip must be tested multiple times to first identify the non-response frequency, rendering the method no better than the original blank test method it seeks to replace and so it is useless in large scale commercial applications.

Essentially, Plaxco's method involves experimentally determining the dose response curve of signal change versus target concentration. For any E-AB sensor this curve will be non-linear irrespective of the bioreceptor, however the Calibration-Free method requires identification of a narrow section of the curve such that a linear line of best fit can be applied to it and utilized as the calibration equation in future tests of unknown target concentrations. Fitting a linear curve to a non-linear dataset will mean that the error in estimated concentration values is quite large and so only a narrow range of concentrations can be measured to produce an estimated concentration accurate to within 20%—the largest acceptable total system error for any commercial diagnostic product—of the target concentration. This range of concentrations that the sensor can measure is typically within 1 order of magnitude of the disassociation constant Kd (which is determined in the Calibration-Free method by globally fitting their calibration equation to a dataset of multiple sensors of the same class).

Thus, to date there are no calibration methods suitable for large scale commercialized aptamer electrochemical sensor products.

SUMMARY OF THE INVENTION

As shown in FIG. 4, the inventors have identified that the unbound/unbound ratio $i_{min1}/i_{min2}$ for any two selected frequencies remains constant across all sensors of a sensor class, regardless of the sensor-to-sensor variations that are expected to occur during manufacturing. The inventors have further identified that the signal ratio from a target-rich solution for any two selected frequencies, $i_1/i_2$, also remains constant across all sensors of a sensor class. The inventors have further identified a linear relationship $Y=(1/Kd)*[T]$ between target concentration [T] and signal ratio function Y (based upon $i_1/i_2$) which can be mathematically determined to produce highly accurate results without the need to apply a linear line of best fit to a non-linear dataset. The unbound/unbound ratio $z=i_{min1}/i_{min2}$, can be determined during development of a new sensor class or manufacturing, and can be used to derive a concentration equation such that when testing in situ, the target solution can be measured at the two designated frequencies and the equation produces accurate and reliable concentration results at the point of use. This derived concentration equation can be used in an analyte testing method that does not require any additional steps to calibrate the sensor, therefore enabling a sensor that is suitable for any commercial use. The name of the calibration method based on this relationship is the Self-Parative Calibration Method.

DETAILED DESCRIPTION

The method is applied to a sensor modified with an aptamer as bioreceptor. Aptamers are oligonucleotides or peptide molecules that bind to a specific target molecule with high affinity to target molecules based on three-dimensional conformations that interact with the complementary target molecules. The more target present in a sample, the more aptamers bind and the larger the average measured signal (faradic discharge current) across the electrode surface when an electrochemical method is applied. The electrochemical method is preferably a pulsed voltammetry method such as square wave voltammetry (SWV) or differential pulse voltammetry (DPV). In these methods, the current response is measured when potential is applied across the working, reference and counter electrodes of the sensor.

Upon binding, some aptamers undergo conformational change. The aptamers for target analyte may be developed using SELEX (Systematic Evolution of Ligands by EXponential enrichment) method, where they are selected for high binding affinity and conformational change of the aptamer whereby it folds (or opens wider) after binding to target. Examples of suitable aptamers for adenosine triphosphate and tobramycin are found in the literature at Liu et al., "Achieving Reproducible Performance of Electrochemical, Folding Aptamer-Based Sensors on Microelectrodes: Challenges and Prospects," Analytical Chemistry 2014, 86, 11417-11424. The aptamer sequence may be further modified to produce a greater structure change by: 1) truncating the aptamer to make it shorter by conducting experiments to approximate the region on the aptamer that binds to target and then removing DNA bases that are not in the binding region; and 2) mismatching bases in the aptamer's structure to make it less stable whereby when the aptamer binds to target the conformational change is more significant. The process of developing the aptamers may require several rounds of testing with the target to ascertain whether the aptamer shows signal change due to structure change.

Aptamers displaying the conformational change are further modified with a redox-active molecule, such as methylene blue (MB) or ferrocene (Fc), on the free end. An aptamer with redox-active molecule at the free end will therefore change the proximity of the redox-active molecule to the substrate depending upon whether it is in a bound state or unbound state. This results in faradic discharge that can be sampled using the electrochemical method.

Figure 6:
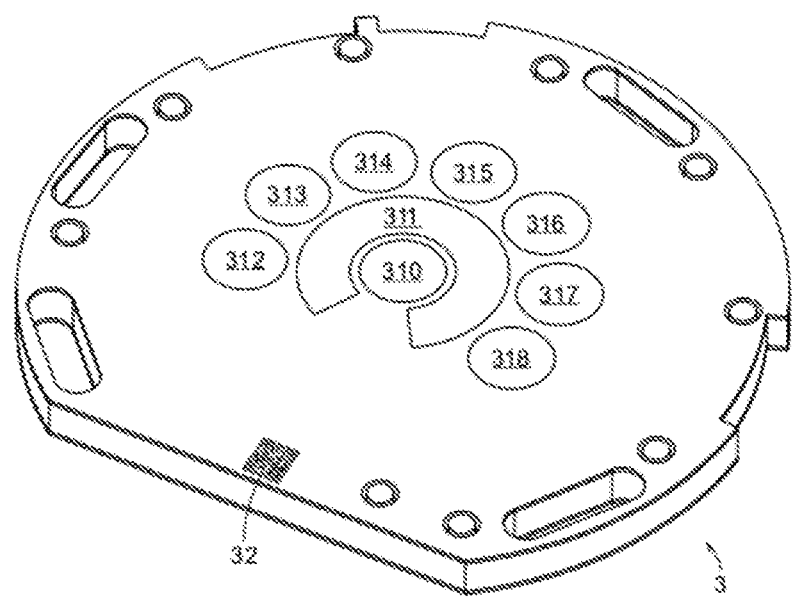
FIG. 6 is an example of an instance of a sensor representing a sensor class.

A sensor class is defined herein as the set of sensors having sufficiently common design characteristics such that all sensors of the selected design will respond similarly when utilized within a selected set of selected assay conditions. For instance, sensors belonging to the same sensor class will have identical electrode structure, substrate composition, aptamers, aptamer composition, type of redox reporter, and will be fabricated according to the same process. As one example, a representative instance of a sensor 3 in a sensor class is depicted in FIG. 6. This sensor class represents all sensors having a reference electrode 310, a counter electrode 311, and working electrodes 312 through 318 positioned as shown. Sensor 3 is a multiplex sensor that can have seven different aptamers each immobilized on a different working electrode, but the aptamers and their location as assigned to each working electrode is identical across the sensor class. The only variations within a sensor class are the variations that manifest due to differences in manufacturing and environmental conditions, but all sensors in the same sensor class are manufactured according to the same process.

Existing biosensor fabrication methods at the time of writing include sputtering, screen-printing and printed circuit board manufacturing. Sputtering and magnetron sputtering use thin film deposit processes. The equipment requires a vacuum to operate, typically nitrogen is used to fill and clean the substrate surface, and the equipment is physically large. Pre-treatment must be applied to the biosensor substrate before the electrode material can be applied to the substrate. The connection between substrate and electrode material relies upon physical adsorption and is therefore not a strong connection. Screen-printing is the only manufacturing process readily available for commercial applications. In this technique the support material can be a soft or flexible material such as plastic. The electrode material is not a solid material, rather it is a powder material and it is also mixed with an adhesive material or solvent. PCB manufacturing involves chemical deposit of the conductive material with a modified surface layer on which is bound the aptamers. While there is an existing global infrastructure supporting this manufacturing method, to date only a few cases of use of PCBs to produce biosensor electrode platform have been attempted for research purposes, because high quality biosensor measurements have not been achievable with this manufacturing method. PCB electrodes show poorer signal than screen printed electrodes and are generally not thought to be suitable for use.

Materials and combinations of materials such as, but not limited to gold, silver, platinum, copper, nickel, carbon, conducting polymer, metal particle, and other conductive materials can be used as the substrate upon which biochemistry can be modified to constitute the electrode. Gold is the most often used surface material for aptamer binding. The aptamers are immobilized on the modified surface layer by covalent bonding the aptamer to the gold surface layer with an active group such as thiol (—SH), carboxyl (—COOH), hydroxyl (—OH) at end (5' or 3'). Modification of the working electrode surface can be achieved via biochemical coupling reaction such as NHS/EDC primary amine group modification or thiol-gold modification based on different materials of the electrode.

In the case of bioreceptor with reversible binding with stoichiometry 1:1, a known formulation of analyte concentration [T] in an electrochemical method yielding output i, can be formulated as:

$$[T] = Kd \frac{i - i_{min}}{i_{max} - i} \quad \text{Equation 1}$$

where $i_{min}$ is the peak height without binding target and $i_{max}$ is the peak height if the sensor molecules are totally bound with target, and Kd is the known measurement of the binding affinity of the aptamer and the target, known in the art as the dissociation constant. E.g., Alexander P. Demchenko, "The problem of self-calibration of fluorescence signal in microscale sensor systems," Lab Chip, 2005, 5, 1210-1223. This calibration equation is only effective if the i, imin, and imax are measured in the same test and in exactly the same experimental conditions, but as discussed in the Background, the problem of calibration is that it is not feasible for all of these measurements to be performed in the same test or at the point of use.

The inventors have identified that the unbound/unbound ratio $i_{min1}/i_{min2}$ for any two selected frequencies remains constant across all sensors of a sensor class, regardless of the sensor-to-sensor variations that are expected to occur during manufacturing. The inventors have further identified that the ratio of obtained signal from a target-rich solution for any two selected frequencies, $i_1/i_2$, also remains constant across all sensors of a sensor class. These results are shown below in Tables 1 and 2 below, as well as in FIG. 4.

TABLE 2

The constant of z (in blank milk)

| Electrodes | Test strip1 | Test strip2 | Test strip3 | Average | SD | RSD |
|---|---|---|---|---|---|---|
| WE1 | 4.482 | 4.206 | 4.239 | Cross test-strips | | |
| WE2 | 4.134 | 4.801 | 4.372 | 4.301 | 0.036 | 0.80% |
| WE3 | 4.284 | 4.003 | 4.525 | Cross all WE | | |
| WE4 | 4.249 | 4.376 | 4.229 | 4.301 | 0.121 | 2.80% |
| WE5 | 4.434 | 4.354 | 4.326 | | | |
| Average | 4.317 | 4.260 | 4.328 | | | |
| SD | 0.127 | 0.115 | 0.106 | | | |
| RSD | 2.33% | 2.69% | 2.51% | | | |

TABLE 2

The variable of i1/i2 at given concentration (78 uM tobramycin in milk)

| Electrodes | Test strip1 | Test strip2 | Test strip3 | Average | SD | RSD |
|---|---|---|---|---|---|---|
| WE1 | 5.663 | 4.925 | 5.431 | Cross test-strips | | |
| WE2 | 5.654 | 5.116 | 5.622 | 5.190 | 0.203 | 3.92% |
| WE3 | 5.240 | 4.765 | 5.120 | Cross all WE | | |
| WE4 | 4.892 | 5.105 | 5.082 | 5.190 | 0.288 | 5.54% |
| WE5 | 5.167 | 4.868 | 5.199 | | | |
| Average | 5.323 | 4.956 | 5.231 | | | |
| SD | 0.297 | 0.136 | 0.205 | | | |
| RSD | 5.58% | 2.75% | 3.88% | | | |

These experimental results drive the derivation of a formula for analyte concentration [T] as follows:

Because the ratio of $i_{max}/i_{min}$, recorded as γ, is constant for a given sensor and condition, we can express the concentration [T] at each working frequency as:

$$\text{Frequency 1:} \quad [T] = Kd \frac{i_1 - i_{min1}}{i_{max1} - i_1} \quad \text{Equation 2}$$

$$\text{Frequency 2:} \quad [T] = Kd \frac{i_2 - i_{min2}}{i_{max2} - i_2}$$

$$\text{Frequency 3:} \quad [T] = Kd \frac{i_3 - i_{min3}}{i_{max3} - i_3}$$

. . . . .

$$\text{Frequency } n: \quad [T] = Kd \frac{i_n - i_{minn}}{i_{maxn} - i_n}$$

Figure 1:
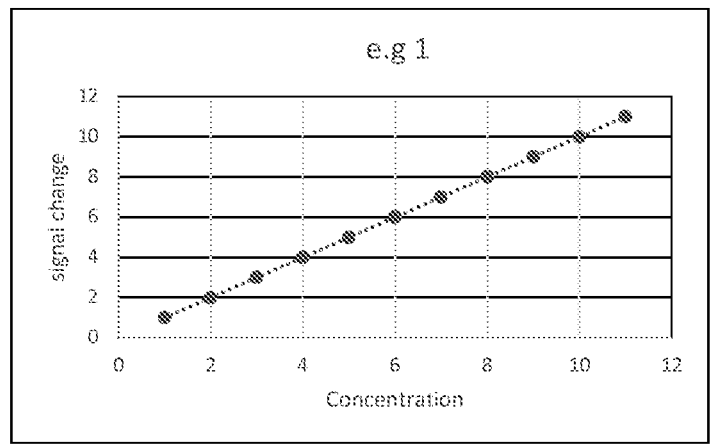
FIG. 1 depicts several graphs showing signal change of different sensors plotted against target concentration.
Figure 1:
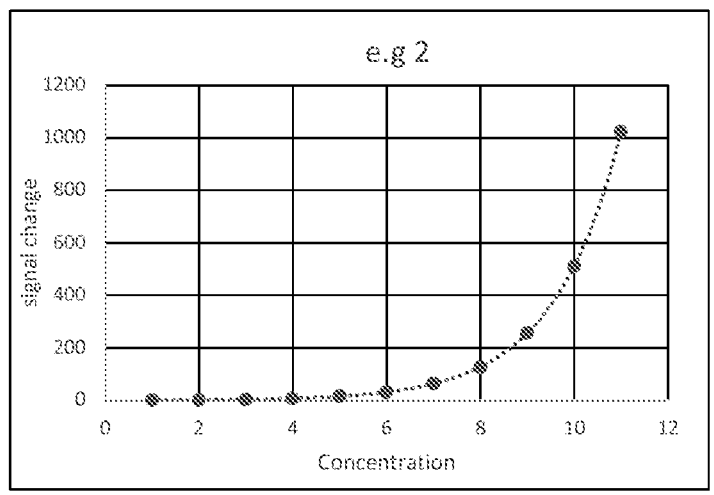
Figure 1:
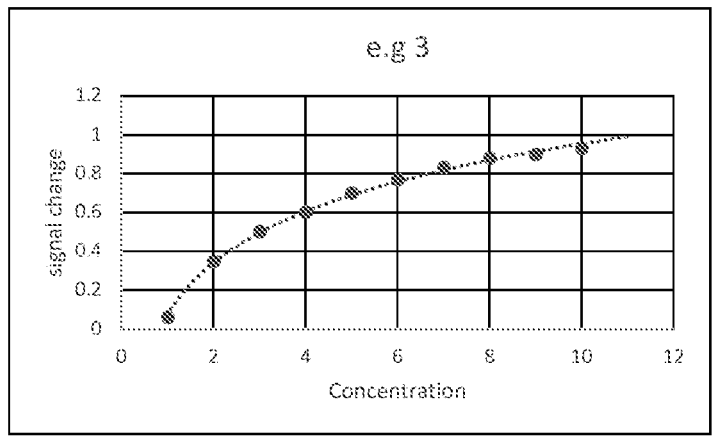
Figure 2:
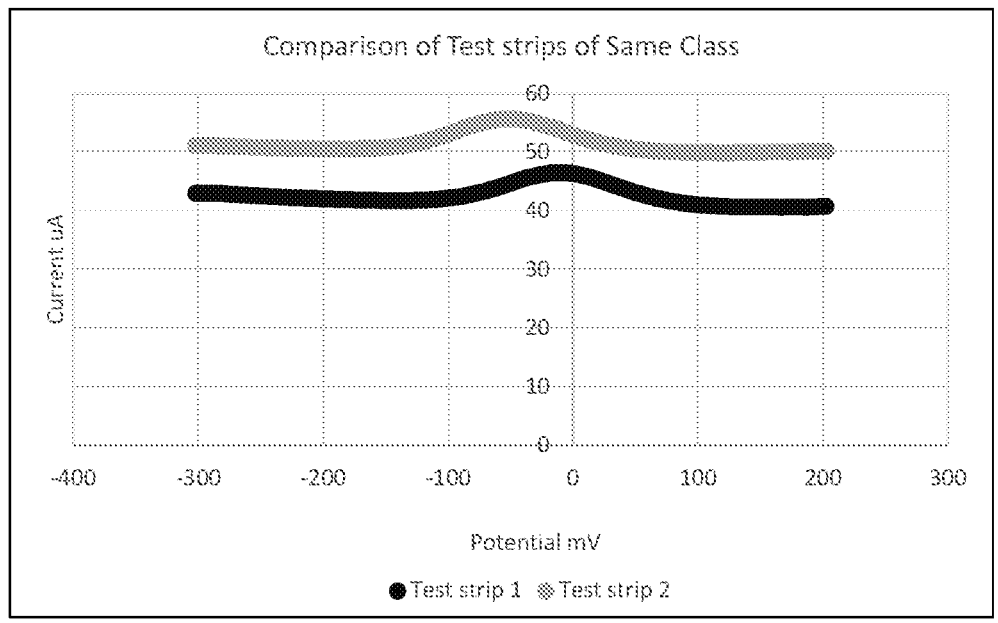
FIG. 2 is a graph of the output when the electrochemical method is performed on two aptamer test strips that have been fabricated in as close a manner as is possible with current manufacturing techniques.
Figure 3:
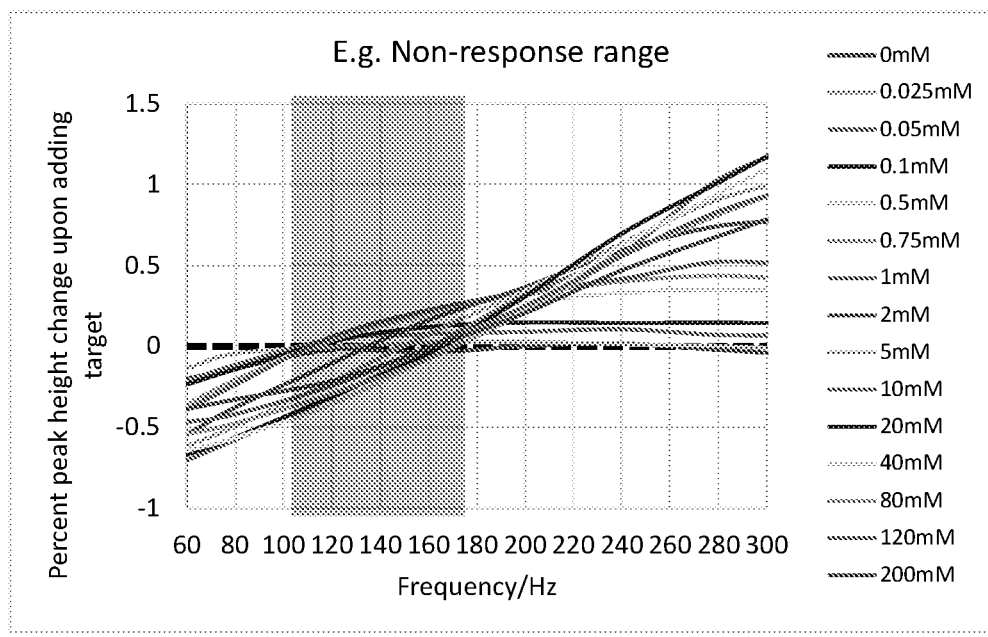
FIG. 3 is a graph of voltammetry peak height change when the electrochemical method is performed at each frequency for different target concentrations (0 mM to 200 mM), showing the "non-response frequency" of Plaxco spanning frequencies from 100 to 180 Hz.
Figure 4:
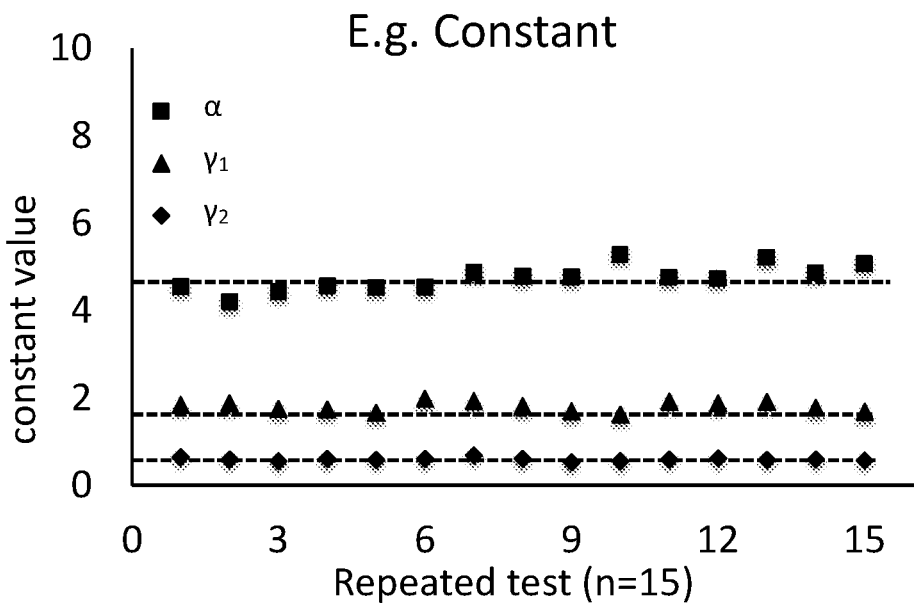
FIG. 4 is a graph plotting the three constants $\gamma_1=i_{max1}/i_{min1}$, $\gamma_2=i_{max2}/i_{min2}$, and $z=i_{min1}/i_{min2}$, which are constant across biosensors in the same sensor class.

In the same test sample, the concentration is constant, therefore:

$$Kd \frac{i_1 - i_{min1}}{i_{max1} - i_1} = Kd \frac{i_2 - i_{min2}}{i_{max2} - i_2} \quad \text{Equation 3}$$

$$\frac{\frac{i_1}{i_{min1}} - 1}{\gamma_1 - i_1/i_{min1}} = \frac{\frac{i_2}{i_{min2}} - 1}{\gamma_2 - i_2/i_{min2}} \quad \text{Equation 4}$$

wherein $\gamma_1$ and $\gamma_2$ are the ratio of $i_{max1}/i_{min1}$ and $i_{max2}/i_{min2}$ respectively. The inventors have further identified that these ratios are constant at any two frequencies, as shown in FIG. 4. Since the $i_{min1}/i_{min2}$, denoted as z, has also been found to be constant (FIG. 4), we have:

$$\frac{i_1 - z*i_{min2}}{\gamma_1 z * i_{min2} - i_1} = \frac{i_2 - i_{min2}}{\gamma_2 i_{min2} - i_2} \quad \text{Equation 5}$$

$$\frac{i_{min2}}{i_2} = \frac{(\gamma_1 - 1)}{(\gamma_1 - \gamma_2)} + \frac{i_1}{i_2} * \frac{(1 - \gamma_2)}{(z\gamma_1 - z\gamma_2)} \quad \text{Equation 6}$$

$$[T] = Kd \frac{\frac{i_2}{i_{min2}} - 1}{\gamma_2 - i_2/i_{min2}} \quad \text{Equation 7}$$

Through the calculation, the final formula can be written as:

$$[T] = Kd \frac{\frac{i_1(\gamma_2 - 1)}{i_2(\gamma_2 - \gamma_1)*z} + \frac{1 - \gamma_1}{\gamma_2 - \gamma_1} - 1}{1 - \gamma_2 * \left(\frac{i_1}{i_2} * \frac{\gamma_2 - 1}{(z\gamma_2 - z\gamma_1)} + \frac{1 - \gamma_1}{\gamma_2 - \gamma_1}\right)} \quad \text{Equation 8}$$

From this formula, $i_1$ and $i_2$ are the only variables that need to be tested in-situ as all other variables are constant and can be calculated for the same sensor class during the initial product development before mass manufacture.

All E-AB sensors utilizing a calibration equation developed upon Equation 1 will result in a non-linear relationship between signal change ($i/i_{min}$) and target concentration. Rather than fitting a linear line of best fit to a non-linear dataset, the inventors have identified that Equation 8 can be manipulated by substitution of Equation 9 to produce Equation 10, a linear relationship between target concentration [T] and signal ratio function Y (which only requires inputs for $i_1/i_2$) which can be mathematically determined to produce highly accurate results.

$$Y = \frac{\frac{i_1(\gamma_2 - 1)}{i_2(\gamma_2 - \gamma_1)*z} + \frac{1 - \gamma_1}{\gamma_2 - \gamma_1} - 1}{1 - \gamma_2 * \left(\frac{i_1}{i_2} * \frac{\gamma_2 - 1}{(z\gamma_2 - z\gamma_1)} + \frac{1 - \gamma_1}{\gamma_2 - \gamma_1}\right)} \quad \text{Equation 9}$$

$$Y = \frac{1}{Kd}[T] \quad \text{Equation 10}$$

Figure 5:
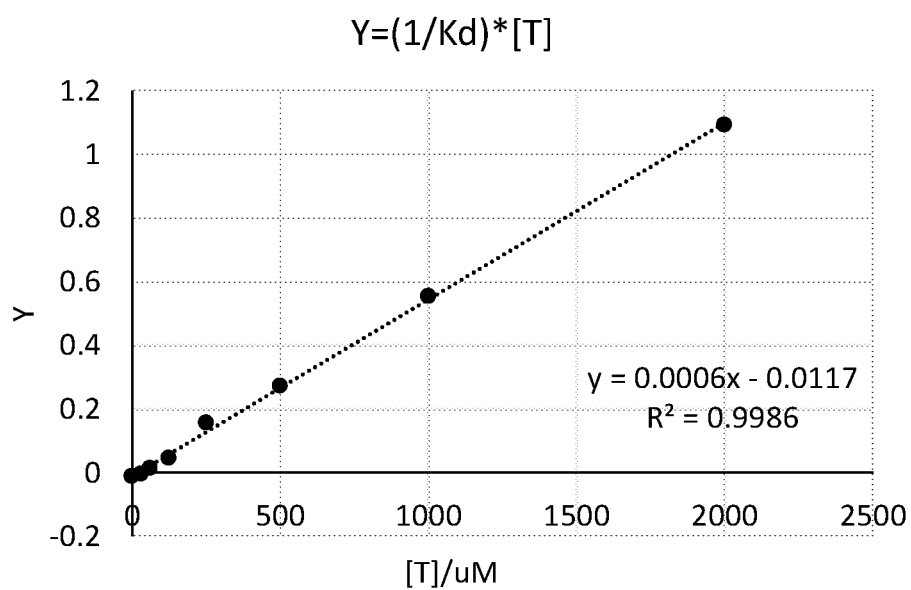
FIG. 5 is the deformation equation or calibration curve of the signal change against concentration [T].

Thus, Equation 10 deformation equation can be calculated and the concentration plot of the Y versus concentration [T] can be visualized with a very low variation error ($R^2 = 0.9986$) as shown in FIG. 5. Equation 10 allows for the detection of wider range of concentrations than is typically achievable with existing calibration methods. Additionally, Kd can be calculated directly from the gradient of the slope of this graph which is a simpler approach.

At the point of use, the working electrode(s) of the sensor need only be sampled at the two frequencies, and these values input to Equation 8 to determine an accurate value for the concentration of analyte. The two frequencies, along with the disassociation constant Kd, $\gamma_1$, $\gamma_2$ and z, may be determined during an initial testing stage of the sensor. The two frequencies are any two frequencies that show signal change in the presence of the analyte, and preferably two frequencies that show maximum amount of signal change. Any two frequencies can be used so long as the peak heights for a target concentration are not the same for the two frequencies. This is an advantage over the Calibration-Free method since the non-response frequency does not have to be determined or used and gives more option with regards to working frequencies that can be used in a commercial sensor. For example, if the aptamer's characteristic non-response frequency is determined to be 40 Hz, this slower frequency will require a longer time for the electrochemical test to complete, especially in a multiplex sensor platform where many electrodes are utilized. The Self-Parative method allows for two high frequencies to be utilized, which can significantly reduce test time.

In practice, the constants and information about the selected frequencies may then be stored in a database containing an identification of each sensor and its associated frequencies and constants. A sensor identification 32 may be physically affixed to the sensor 3 to facilitate scanning and retrieval of the constants before operation of the test. Thus, an example of application of the Self-Parative Calibration Method is as follows:

Step 1: The sensor is inserted into or otherwise operatively connected to an electronic device configured to activate a pulsed voltammetric test to sample current at each working electrode.

Step 2: Sample is deposited over the working electrodes and allowed some time for the aptamers to bind to target present in the sample.

Step 3: Upon receipt of an instruction to initiate, the electronic device performs the voltammetry test at the first frequency associated with the sensor, obtaining a first current value $i_1$.

Step 4: The electronic device performs the voltammetry test at the second frequency associated with the sensor, obtaining a second current value $i_2$.

Step 5: The current values $i_1$ and $i_2$ are input into Equation 9, along with the constants associated with the sensor to find Y which, can be input into Equation 10, whereby analyte concentration [T] is calculated.

Thus, analyte concentration can be measured at point of use without an additional and cumbersome blank test. Moreover, manufacturing time of the sensor is not significantly affected by blank tests for each sensor, which moreover may not prove reliable once decay and shelf-life has been factored in, and which would not be appropriate for single-use sensors.

The invention claimed is:

1. A method of measuring the concentration of an analyte in sample presented to a sensor modified with an aptamer as bioreceptor, the sensor belonging to a sensor class, the method comprising the steps of:
   applying a pulsed voltammetric electrochemical method at a first frequency to obtain a first current value $i_1$;
   applying the electrochemical method at a second frequency to obtain a second current value $i_2$, wherein the first frequency and the second frequency generate a first and a second current response, respectively, when the electrochemical method is applied to any sensor of the sensor class that is modified with the aptamer, and said first and second current response are non-zero and not equal;

calculating the concentration of the analyte [T] by the equation $$[T] = Kd \frac{\frac{i_1}{i_2} \frac{(\gamma_2 - 1)}{(\gamma_2 - \gamma_1) * z} + \frac{1 - \gamma_1}{\gamma_2 - \gamma_1} - 1}{1 - \gamma_2 * \left( \frac{i_1}{i_2} * \frac{\gamma_2 - 1}{(z\gamma_2 - z\gamma_1)} + \frac{1 - \gamma_1}{\gamma_2 - \gamma_1} \right)}$$

wherein Kd is a dissociation constant for any sensor of the sensor class that is modified with the aptamer, $\gamma_1$ is equal to a ratio of a current response of target-saturated to target-free sample when the electrochemical method is applied at the first frequency for any sensor of the sensor class that is modified with the aptamer, $\gamma_2$ is equal to a ratio of a current response of target-saturated to target-free sample when the electrochemical method is applied at the second frequency for any sensor of the sensor class that is modified with the aptamer, and z is equal to a ratio of a current response of target-free sample when the electrochemical method is applied at the first frequency to a current response of target-free sample when the electrochemical method is applied at the second frequency for any sensor of the sensor class that is modified with the aptamer.

2. The method of claim 1 wherein the sensor class is comprised of a multiplex sensor layout having a counter electrode, a reference electrode, and a plurality of working electrodes.

3. The method of claim 1 wherein the sensor class is comprised of PCB-printed electrodes.

4. The method of claim 2 wherein the sensor class is comprised of PCB-printed electrodes.

5. The method of claim 1 wherein the aptamer is selected to exhibit conformational change, namely changing proximity of the aptamer to the sensor, in the presence of an analyte.

6. The method of claim 2 wherein the aptamer is selected to exhibit conformational change, namely changing proximity of the aptamer to the sensor, in the presence of an analyte.

7. The method of claim 3 wherein the aptamer is selected to exhibit conformational change, namely changing proximity of the aptamer to the sensor, in the presence of an analyte.

* * * * *